(12) United States Patent
Lee et al.

(10) Patent No.: US 10,869,941 B2
(45) Date of Patent: Dec. 22, 2020

(54) GAS-GENERATING POLYMER MICELLS AND MANUFACTURING METHOD OF THE SAME

(71) Applicant: INDUSTRY-UNIVERSITY COOPERATION FOUNDATION HANYANG UNIVERSITY, Seoul (KR)

(72) Inventors: Kuen Yong Lee, Seoul (KR); Eun Ju Jeong, Seoul (KR)

(73) Assignees: INDUSTRY-UNIVERSITY COOPERATION; FOUNDATION HANYANG UNIVERSITY

( * ) Notice: Subject to any disclaimer, the term of this patent is extended or adjusted under 35 U.S.C. 154(b) by 0 days.

(21) Appl. No.: 15/933,143

(22) Filed: Mar. 22, 2018

(65) Prior Publication Data

US 2018/0280548 A1 Oct. 4, 2018

(30) Foreign Application Priority Data

Mar. 22, 2017 (KR) .................. 10-2017-0036127
Mar. 21, 2018 (KR) .................. 10-2018-0032650

(51) Int. Cl.
| | | |
|---|---|---|
| *A61K 49/22* | (2006.01) | |
| *A61K 9/107* | (2006.01) | |
| *A61K 9/51* | (2006.01) | |
| *A61K 47/34* | (2017.01) | |

(52) U.S. Cl.
CPC .......... *A61K 49/227* (2013.01); *A61K 9/1075* (2013.01); *A61K 9/5192* (2013.01); *A61K 47/34* (2013.01); *A61K 49/223* (2013.01); *A61K 2123/00* (2013.01)

(58) Field of Classification Search
CPC .... A61K 49/227; A61K 49/223; A61K 47/34; A61K 9/1075; A61K 9/5192; A61K 2123/00

See application file for complete search history.

(56) References Cited

FOREIGN PATENT DOCUMENTS

| JP | 2002128744 | * | 5/2002 | ............ C07C 69/96 |
|---|---|---|---|---|
| KR | 10-2009-0101758 | | 9/2009 | |
| KR | 10-2014-0080084 | | 6/2014 | |
| KR | 20140080084 | * | 6/2014 | ............ A61K 47/30 |
| KR | 10-2014-0037298 | | 11/2014 | |

OTHER PUBLICATIONS

Banno et al., "Synthesis and Properties of Green Sustainable Carbonate-type Nonionics Containing Polyoxyethylene Chains", Journal of Oleo Science. 60, (3) 117-126 (2011).
Korean Office Action for application No. 2019-047934351, dated Jul. 3, 2019, 6 pages (in Korean language).
IUPAC International Conference on Advanced Polymeric Materials: Commemorating the 40th Anniversary of the Polymer Society of Korea (PSK), Published Oct. 4, 2016, "Preparation and characterization of gas-generating polymeric micelles for ultrasonography", 3 pages.

* cited by examiner

*Primary Examiner* — Michael G. Hartley
*Assistant Examiner* — Leah H Schlientz
(74) *Attorney, Agent, or Firm* — Adsero IP

(57) ABSTRACT

The present invention relates to a gas-generating micelle prepared by coupling a polyethylene glycol derivative and an alkyl chloroformate. The gas-generating micelles according to the present invention are circulated in the body and deposited on the disease site to generate carbon dioxide, and thus a more enhanced ultrasonic diagnostic image can be obtained.

3 Claims, 9 Drawing Sheets
(9 of 9 Drawing Sheet(s) Filed in Color)

[FIG. 1]
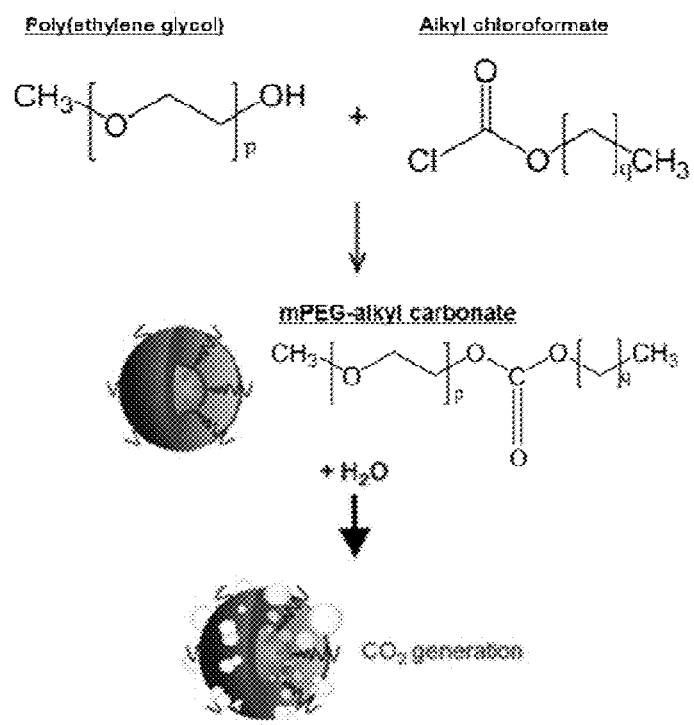
[FIG. 2]
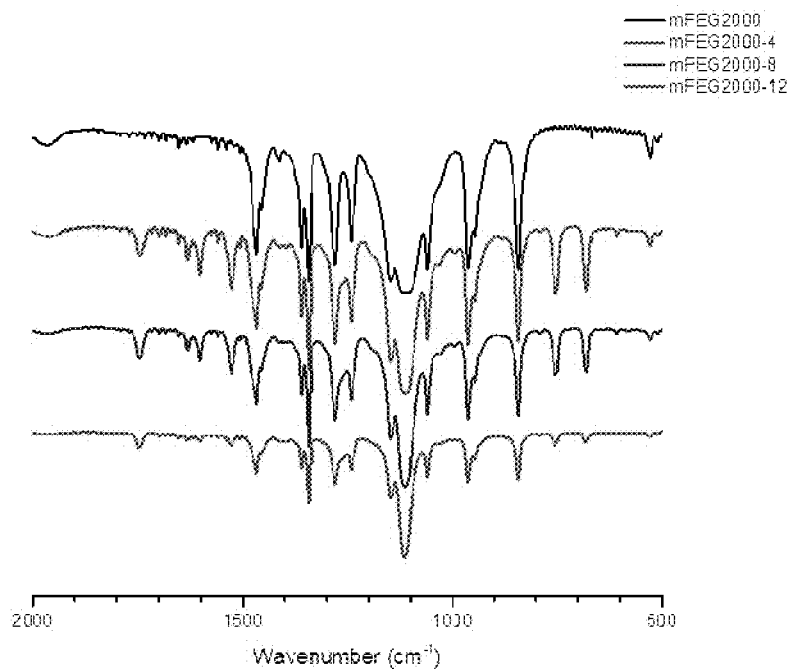

[FIG. 3]
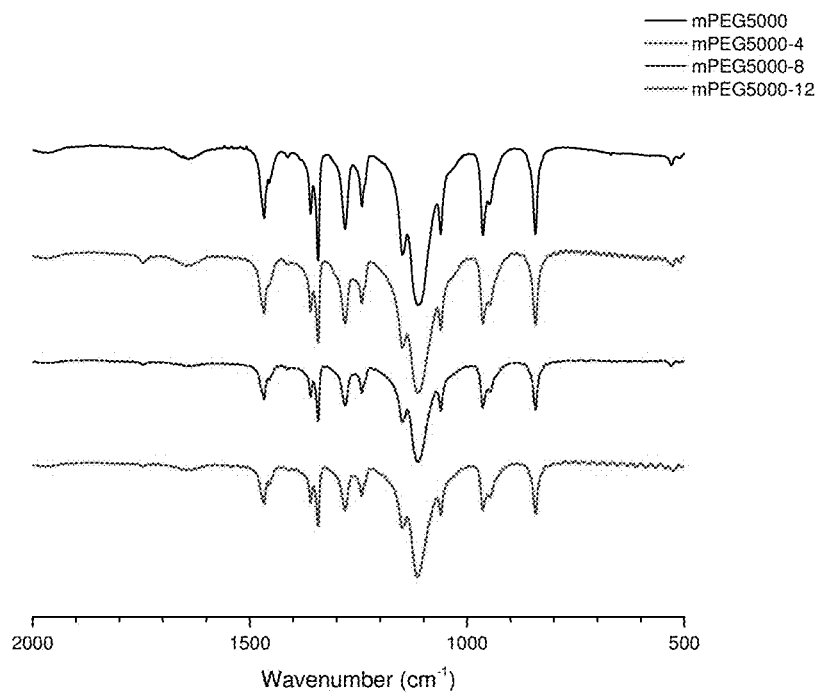
[FIG. 4]
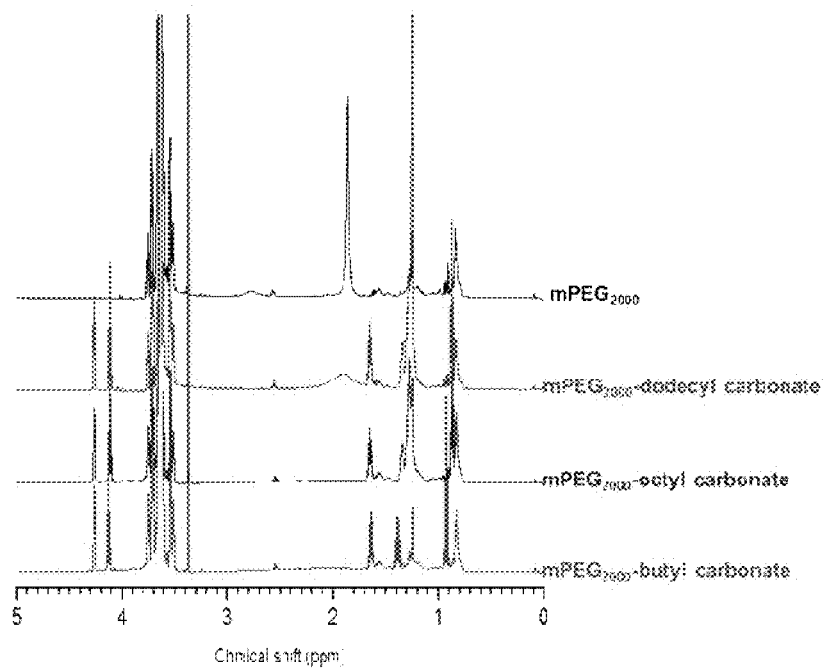

[FIG. 5]
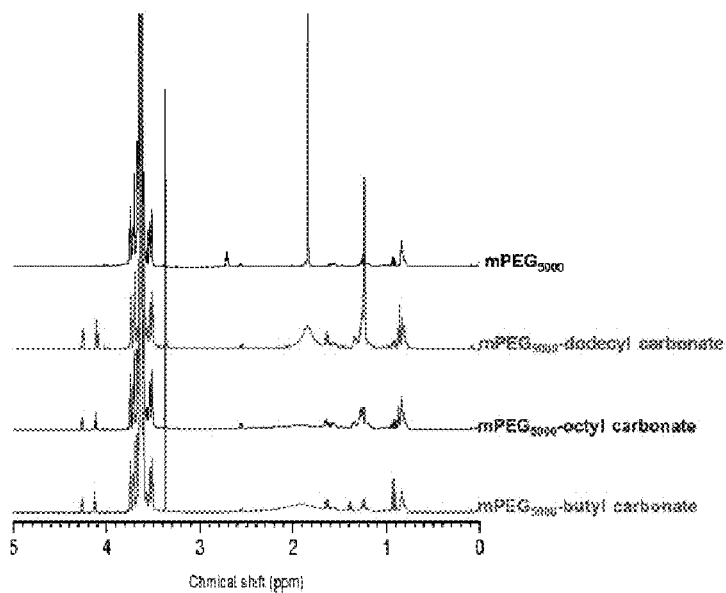
[FIG. 6]
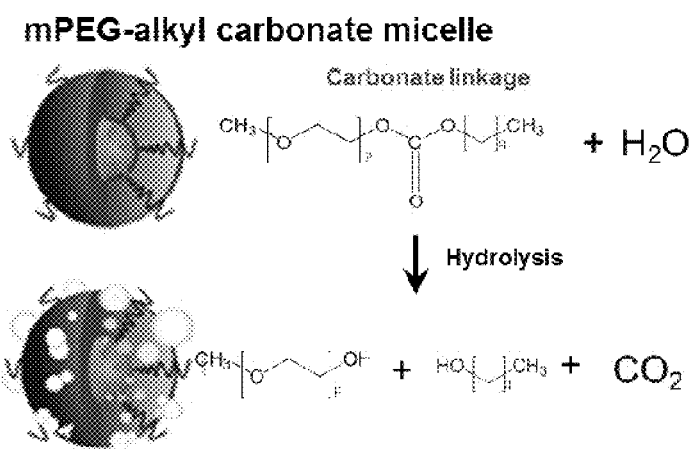
[FIG. 7]
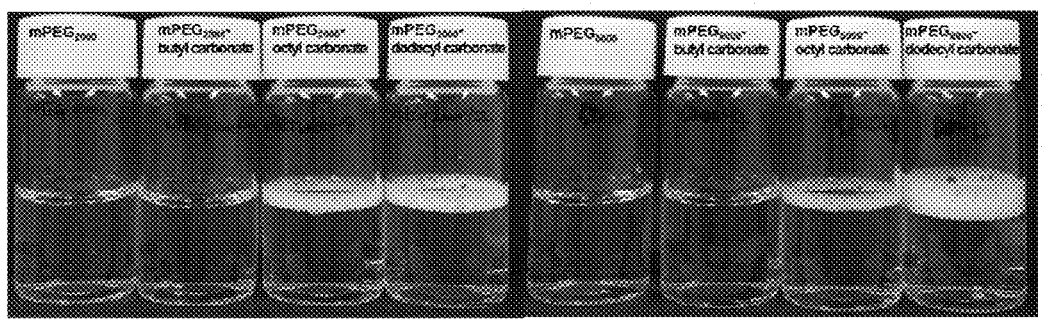

[FIG. 8]
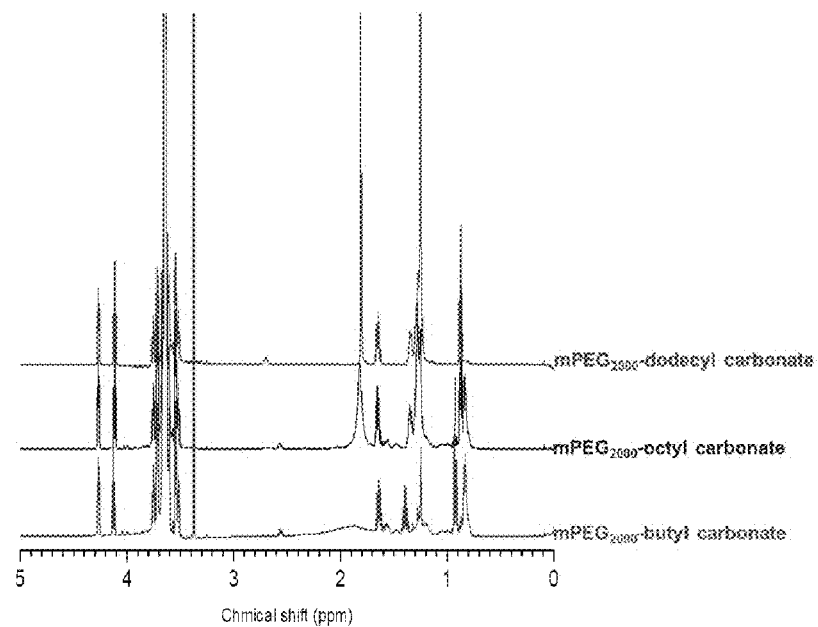
[FIG. 9]
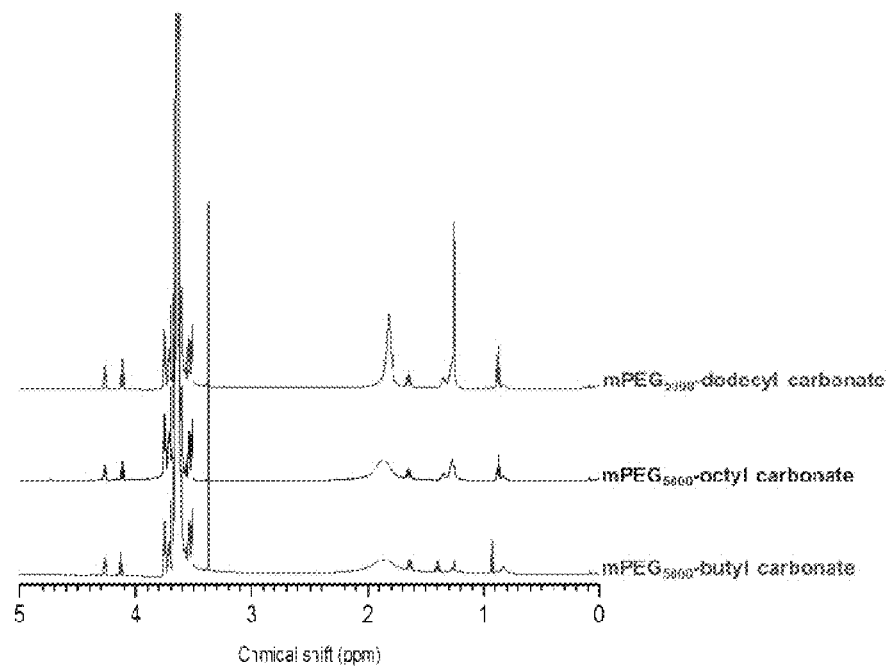

[FIG. 10]
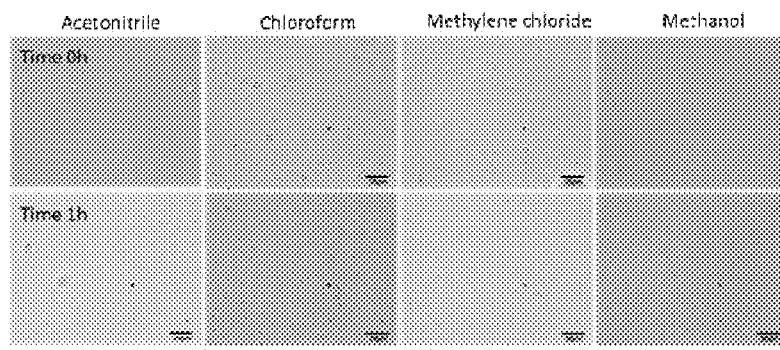
[FIG. 11]
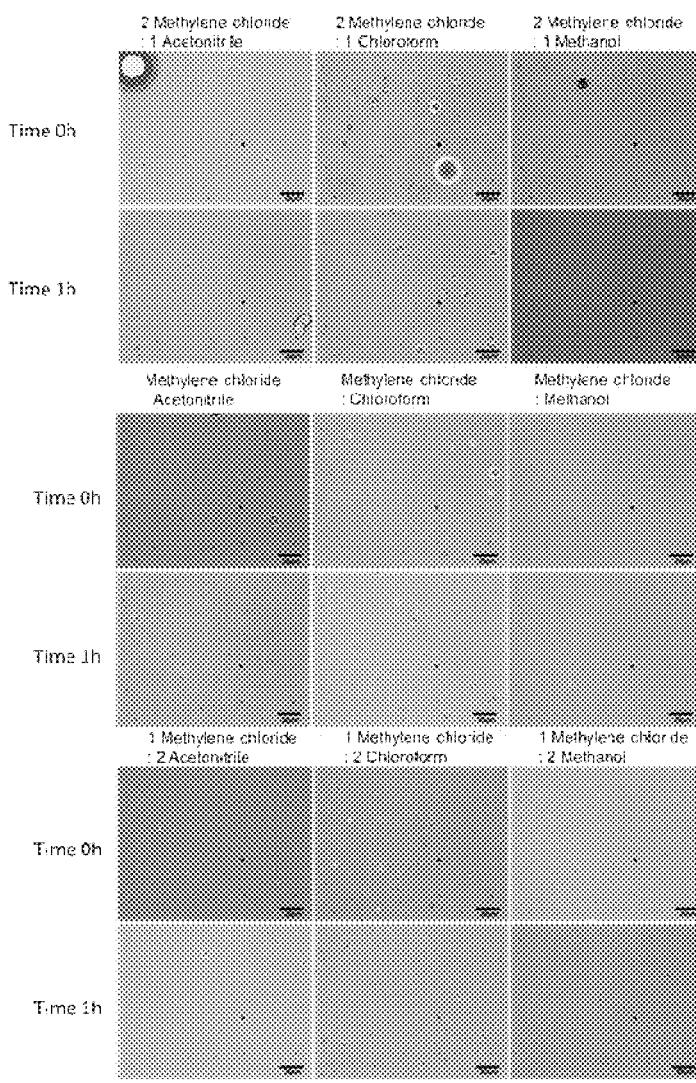

[FIG. 12]
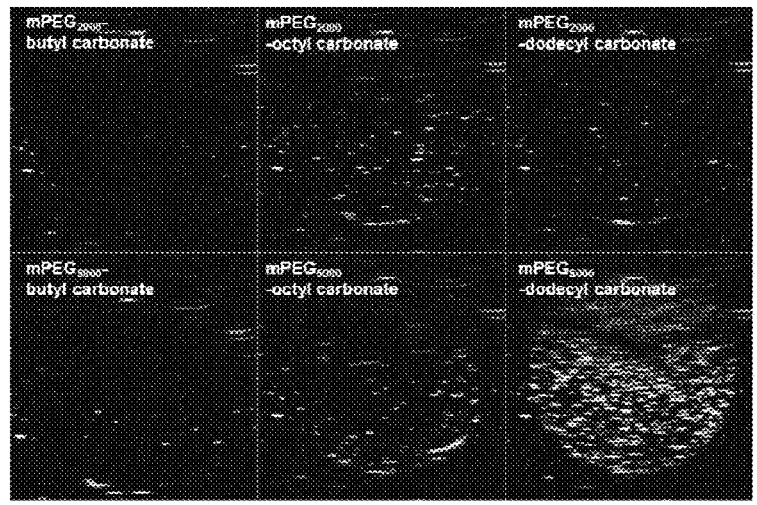
[FIG. 13]
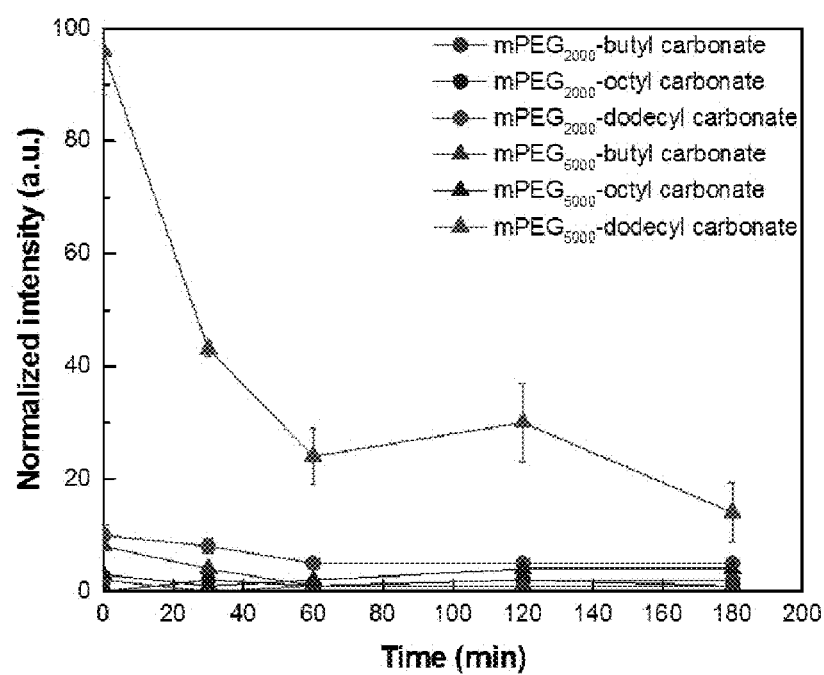

[FIG. 14]
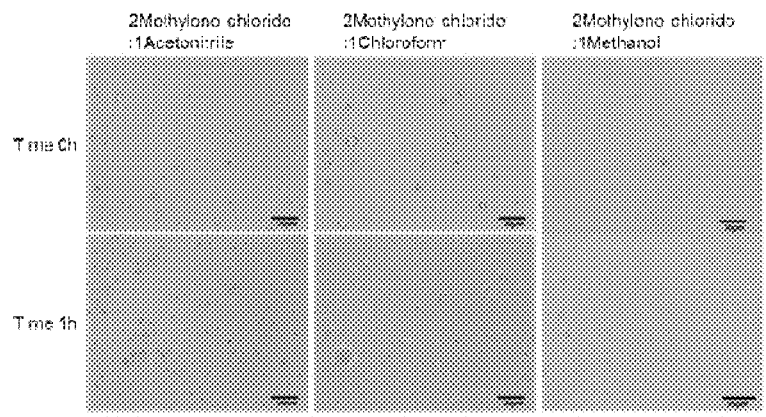
[FIG. 15]
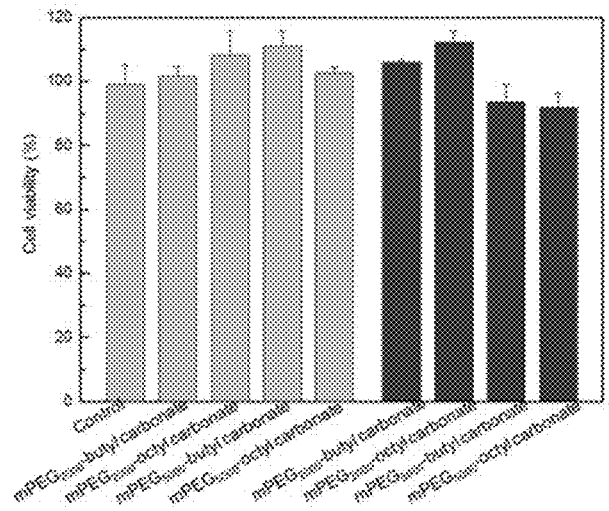

[FIG. 16]
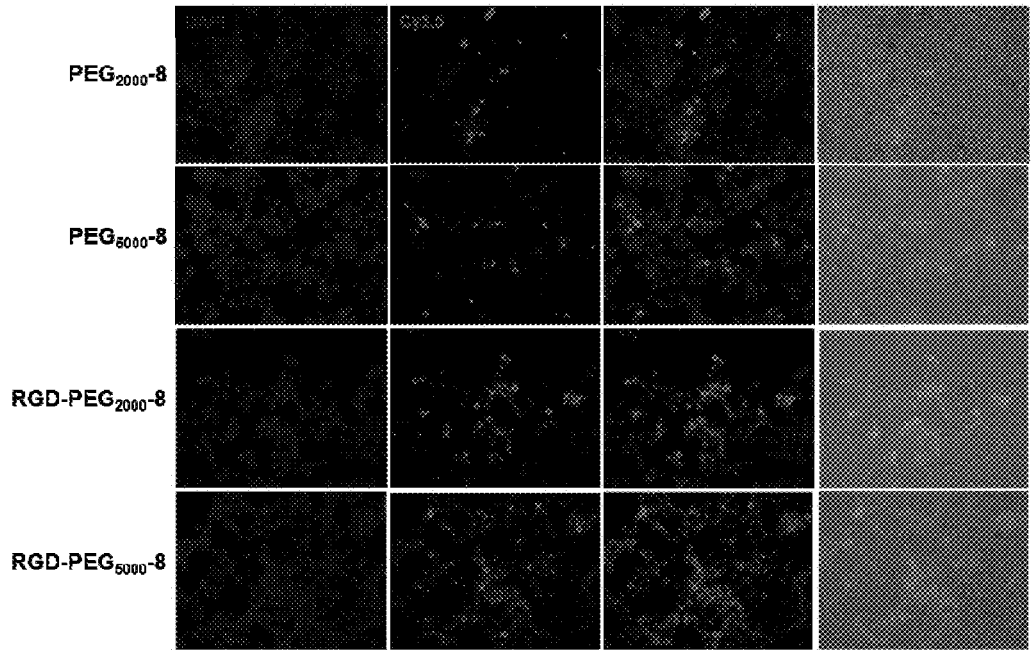
[FIG. 17]
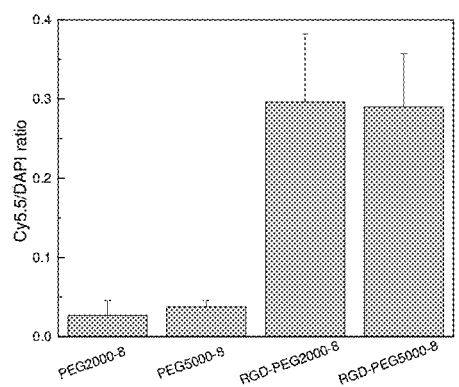

[FIG. 18]
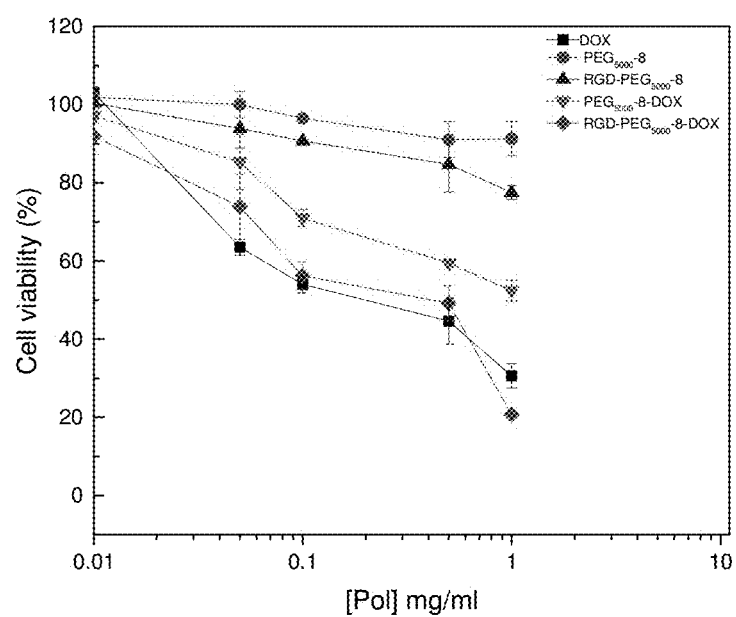

GAS-GENERATING POLYMER MICELLS AND MANUFACTURING METHOD OF THE SAME

CROSS-REFERENCE TO RELATED APPLICATION

This application claims priority to and the benefit of Korean Patent Application No. 2017-0036127, filed on Mar. 22, 2017, the disclosure of which is incorporated herein by reference in its entirety.

BACKGROUND

1. Field of the Invention

The present invention relates to a gas-generating micelle prepared by coupling a polyethylene glycol derivative and an alkyl chloroformate.

2. Discussion of Related Art

Many contrast agents have been extensively developed, and the contrast agents are being used in clinical applications such as X-rays, ultrasound, MR, CT, and PET [Journal of Clinical Oncology 2008; 26(24):4012-4021, European Journal of Nuclear Medicine 2000; 27(6):619-627, Expert Opinion on Drug Metabolism & Toxicology 2009; 5(4):403-416]. The toxicity of the contrast agents resulting in nephrotoxicity, vomiting, alopecia, renal disorders, nephropathy, or nephrogenic system fibrosis has limited the clinical application of the contrast agents [Clinical Journal of the American Society of Nephrology 2007; 2(2):264-267, Investigative Radiology 2008; 43(2):141-144]. Although the toxicity of contrast agents may be suppressed by polymer coating and target-ligand conjugation, potential toxicity still remains.

Recently, non-toxic carbon dioxide gas has attracted significant attention as a contrast agent [European Journal of Radiology 2006; 60(3):324-330, Pharmaceutical Research 2010; 27(1):1-16, Artificial Cells, Blood Substitutes and Biotechnology 1988; 16(1-3):411-420].

Ultrasonic images are obtained by acoustic signals resulting from scattering or reflection of sound at 20 kHz or more and are used to anatomically and functionally image tissues in the body [Heart 1997; 77(5):397-403, European Radiology 2001; 11(8):1316-1328, Ultrasonic Imaging 1979; 1(3): 265-279]. Also, an ultrasound imaging technique has attractive characteristics as a diagnostic tool, such as a non-insertion or non-invasive nature, convenience, an ability to produce an image in real time, and cost-effectiveness [Current Opinion in Pulmonary Medicine 2003; 9(4):282-290].

Microbubbles have been applied as ultrasound contrast agents, but they are inherently unstable in the circulation of blood when administered to the human body and are limited when used in vascular invasion due to their large size, measuring in the order of micrometers. In particular, microbubbles have difficulty in disease-specific diagnosis [Journal of Biomaterials Science, Polymer Edition 2011; 22(4-6):417-428] and in cancer tissue invasion or the like, and thus there is a limitation in use for imaging cancer tissue. Also, it is difficult for microbubbles to function as bioactive molecules.

PATENT DOCUMENTS

1. Korean Registered Patent No. 10-1462723
2. Korean Laid-Open Patent Publication No. 10-2009-0101758

SUMMARY OF THE INVENTION

Microbubbles as conventional ultrasound contrast agents are unstable in blood such that the concentration of microbubbles that can reach a site to be diagnosed is low, and thus it is difficult to carry out precise diagnosis. Also, the membrane of a microbubble mainly consists of a lipid, which makes it difficult to carry out disease-specific diagnosis through the introduction of a ligand targeting a specific disease.

In order to solve the above problems, the present inventors prepared gas-generating nanoparticles which, unlike conventional microbubble ultrasound contrast agents and gas-loaded ultrasound contrast agents, are circulated in the body and deposited on the disease site to generate carbon dioxide, and thus completed the present invention.

Therefore, it is an object of the present invention to provide a gas-generating micelle including a compound represented by Formula 1.

It is another object of the present invention to provide a composition for contrast ultrasound imaging including the gas-generating micelle.

It is still another object of the present invention to provide a composition for inducing cell necrosis through causing damage to a cell, which includes the gas-generating micelle.

It is yet another object of the present invention to provide a drug delivery composition including the gas-generating micelle carrying a drug.

It is yet another object of the present invention to provide a method of preparing a gas-generating micelle including a compound represented by Formula 1, which includes mixing polyethylene glycol and an alkyl chloroformate to synthesize a polyethylene glycol derivative; and dissolving the polyethylene glycol derivative in one solvent selected from acetonitrile, methylene chloride, chloroform, and methanol or in a solvent mixture of two or more selected therefrom and then evaporating the solvent(s).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will become more apparent to those of ordinary skill in the art by describing in detail exemplary embodiments thereof with reference to the attached drawings, in which:

FIG. 1 is a schematic diagram for preparing a gas-generating micelle through the introduction of a carbonate group;

FIGS. 2 and 3 are graphs analyzing polyethylene glycol-alkyl carbonate through Fourier transform-infrared spectroscopy (FT-IR);

FIGS. 4 and 5 are graphs analyzing polyethylene glycol-alkyl carbonate through nuclear magnetic resonance (NMR);

FIG. 6 is a schematic diagram of a process of generating carbon dioxide gas through hydrolysis of a gas-generating micelle according to the present invention under aqueous conditions;

FIG. 7 is an image illustrating the generation of carbon dioxide gas through hydrolysis of polyethylene glycol-alkyl carbonate;

FIG. 8 is a graph illustrating the hydrolysis capacity of polyethylene glycol2000-alkyl carbonate through H-NMR;

FIG. 9 is a graph illustrating the hydrolysis capacity of polyethylene glycol5000-alkyl carbonate through H-NMR;

FIG. 10 is an image illustrating a difference in amount of gas generated by polyethylene glycol5000-dodecyl carbonate micelles according to the type of a single organic solvent used;

FIG. 11 is an image illustrating a difference in amount of gas generated by polyethylene glycol5000-dodecyl carbonate micelles according to the type of a solvent mixture used;

FIG. 12 is an image illustrating the evaluation result of the ultrasonic diagnosis capacity of a gas-generating micelle according to the present invention using ultrasound equipment;

FIG. 13 is a graph illustrating the quantitative analysis result of ultrasound images of gas-generating micelles according to the present invention using ultrasound equipment;

FIG. 14 is an image illustrating a difference in amount of gas generated by polyethylene glycol2000-octyl carbonate according to the type of a solvent mixture used;

FIG. 15 is a graph illustrating the cytotoxicity results of polyethylene glycol-alkyl carbonate and micelles prepared using the same;

FIG. 16 is a set of images of ligand-introduced micelles as observed by a fluorescence microscope (TE2000-E; Nikon);

FIG. 17 is a graph of the evaluation result of an intracellular transmission capacity of ligand-introduced micelles; and FIG. 18 is a graph of the evaluation result of a cell death effect of drug-carrying micelles.

DETAILED DESCRIPTION OF EXEMPLARY EMBODIMENTS

Hereinafter, the present invention will be described with reference to examples and comparative examples in detail. However, the present invention is not limited to these examples.

In order to accomplish the above objectives, there is provided a gas-generating micelle including a compound represented by the following Formula 1.

[Formula 1]

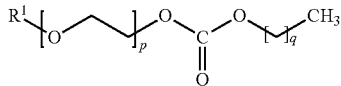

In Formula 1,

R1 is a C1 to C2 alkyl group, H, —NH2, or COOH, p is an integer ranging from 12 to 227, and q is an integer ranging from 2 to 14.

In one embodiment, q in the compound may be an integer ranging from 4 to 10, 4 to 8, 6 to 10, or 8 to 10.

In one embodiment, the micelle may have a diameter of 150 to 500 nm.

The term "micelle" used herein generally refers to a spherical compound consisting of low molecular weight compounds having amphiphilicity, for example, having both a hydrophilic group and a hydrophobic group. The micelle is thermodynamically stable. When a water-insoluble (hydrophobic) drug is dissolved in a compound with the micelle structure, the drug is present inside the micelle. Since such a micelle can release the drug in a target-oriented manner in response to a change in temperature or pH in the body, the micelle is highly applicable as a carrier for drug delivery. However, it is important for the micelle to stably carry the drug until it reaches a specific disease (e.g., cancer) site and releases the drug in the blood vessel, when intravascularly administered to the human body.

The micelle according to the present invention includes a compound including a carbonate group formed by conjugating an alkyl chloroformate and a hydroxy group of a polyethylene glycol derivative. Hereinafter, this compound will be referred to as a synthetic polymer in the present invention.

Specifically, the micelle has a carbonate linkage between an alkyl chloroformate in a hydrophobic core and a hydrophilic polyethylene glycol derivative on a surface (or shell). Therefore, the micelle has a form in which an alkyl chloroformate is inside the micelle and a polyethylene glycol derivative is on the surface of the micelle.

In one embodiment, the micelle may include a target-oriented ligand bound to a surface thereof. A ligand may be bound to the terminal site of the polyethylene glycol derivative present on the surface of the micelle to form a strong bond. Due to characteristics of a ligand, the micelle according to the present invention may have an orientation toward a target. The term "ligand" used herein refers to a molecule which binds to a ligand-binding protein to cause a structural change. The ligand may be any one of a sugar, an amino acid, a protein, a lipid, an organic acid, a metal or a metal ion, an oxide, a hydroxide or a conjugate thereof, an inorganic ion, an amine or a polyamine, and a vitamin, but the present invention is not limited thereto. There is no limit to the type of ligand that may be used as long as it is a type that is specifically bound to a receptor to be targeted.

In one embodiment of the present invention, the micelle including a carbonate group according to the present invention generates carbon dioxide gas by hydrolytic cleavage of a carbonate group of the micelle under aqueous conditions (FIG. 6).

In one embodiment, the present invention provides a composition for contrast ultrasound imaging including the gas-generating micelle. As described above, the gas-generating micelle according to the present invention may generate carbon dioxide under aqueous conditions and, being in the form of a nanoparticle, may be circulated in the body and deposited on the disease site to generate a gas. Therefore, it is possible to generate a larger amount of gas in a targeted disease site, and thus a more enhanced diagnostic image for the disease can be obtained.

In one embodiment of the present invention, the ultrasonic diagnosis capacity of the gas-generating micelle according to the present invention was evaluated using ultrasound equipment. As a result, it was confirmed that an ultrasound imaging effect of micelles prepared using polyethylene glycol-alkyl carbonate was excellent. In particular, polyethylene glycol5000-dodecyl carbonate had a contrast ultrasound imaging effect superior to that of other synthetic polymer micelles (FIG. 12).

In another embodiment, the present invention provides a composition for inducing cell necrosis through causing damage to a cell, which includes the gas-generating micelle.

When it is intended to generate carbon dioxide gas using the gas-generating micelle according to the present invention, the causing of damage to a cell may be controlled such that the gas is generated after the micelle is introduced into the cell, by adjusting a time for which the gas is generated and an amount of the gas generated by controlling a structure of the gas-generating micelle.

In one embodiment of the present invention, in order to evaluate a cell damaging effect of the gas-generating micelle according to the present invention, a micelle prepared using a single organic solvent or a solvent mixture was observed through optical imaging. As a result, it was determined that an amount of gas generated by the micelle particle varied depending on the type of a single solvent or the type and mixing ratio of a solvent mixture (FIGS. 10 and 11).

In still another embodiment, the present invention provides a drug delivery composition including the gas-generating micelle carrying a drug. The micelle according to the present invention carries a drug therein, and thus may be used as an effective drug delivery composition. The drug delivery composition according to the present invention may maximize the efficacy of a drug through the generation of gas. In particular, the drug delivery composition may maximize the efficacy of a drug through the generation of gas in an aqueous environment. The drug delivery composition may improve a drug releasing capacity by generating a gas in an aqueous environment and may efficiently deliver a drug and maximize the efficacy of a drug.

Therefore, the drug delivery composition may additionally produce a therapeutic effect through drug delivery while inducing cell necrosis.

In one embodiment of the present invention, the drug may be a chemical drug, a protein, a peptide, or a nucleotide. There is no specific limit to the type of chemical drug that may be used, and a drug having an effect of suppressing the generation of cancer cells, suppressing or delaying the growth of cancer cells, treating cancer, suppressing metastasis according to migration and infiltration of cancer cells, or treating cancer stem cells may be used. There is no specific limit to the protein or the peptide that may be used, and a hormone and an analog thereof, an enzyme, an enzyme inhibitor, a signal transduction protein or a portion thereof, an antibody or a portion thereof, a single chain antibody, a binding protein or a binding domain thereof, an antigen, an adhesion protein, a structural protein, a regulatory protein, a toxic protein, a cytokine, a transcriptional regulatory factor, a blood coagulation factor, a vaccine, or the like may be used.

According to one aspect of the present invention, the present invention provides a method of preparing a gas-generating micelle including a compound represented by the following Formula 1, which includes mixing polyethylene glycol and an alkyl chloroformate to synthesize a polyethylene glycol derivative; and dissolving the polyethylene glycol derivative in one solvent selected from acetonitrile, methylene chloride, chloroform, and methanol or in a solvent mixture of two or more selected therefrom and then evaporating the solvent(s).

[Formula 1]

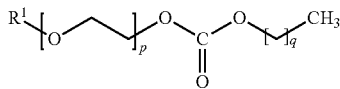

In Formula 1, R1 is a C1 to C2 alkyl group, H, —NH2, or COOH, p is an integer ranging from 12 to 227, and q is an integer ranging from 2 to 14.

In one embodiment, q in the compound may be an integer ranging from 4 to 10, 4 to 8, 6 to 10, or 8 to 10.

In one embodiment, the solvent mixture may be a solvent mixture of methylene chloride and acetonitrile, chloroform, or methanol, and a mixing ratio thereof, i.e., a mixing ratio of methylene chloride and acetonitrile, chloroform, or methanol may be, but is not limited to, 3 to 1:1 to 3, 2 to 1:1 to 2, or 2:1.

In one embodiment, the polyethylene glycol may have a number average molecular weight (Mn) of 550 to 10,000 g/mol.

Hereinafter, the method of preparing a gas-generating micelle according to the present invention will be described in detail.

1. Preparation of Polyethylene Glycol-Alkyl Carbonate Synthetic Polymer

Prior to the preparation of a micelle, a synthetic polymer for a micelle was first prepared.

First, polyethylene glycol and an alkyl chloroformate were separately dissolved in acetonitrile to prepare a polyethylene glycol solution and an alkyl chloroformate solution. The alkyl chloroformate solution was added to the polyethylene glycol solution, and the mixture was stirred. To the mixture thus stirred, pyridine was added and reacted to prepare polyethylene glycol-alkyl carbonate.

In one embodiment, a polyethylene glycol solution may be prepared by dissolving 0.2 to 0.8 mmol of polyethylene glycol in 2 to 6 ml of acetonitrile, and an alkyl chloroformate solution may be prepared by dissolving 1 to 3 mmol of an alkyl chloroformate in 3 to 7 ml of acetonitrile.

In one embodiment, the alkyl chloroformate solution may be added to the polyethylene glycol solution, and then the mixture may be stirred for 2 to 10 minutes, 3 to 8 minutes, or 4 to 6 minutes, but the present invention is not limited thereto. For example, the stirring may be carried out for 5 minutes.

In one embodiment, 1.5 to 3.5 mmol of pyridine may be added to the mixture thus stirred, and reacted at 0 to 5° C. for 20 to 40 minutes and then at room temperature for 24 hours to prepare polyethylene glycol-alkyl carbonate.

Polyethylene glycol used in the present invention may have, but is not limited to, a number average molecular weight of 550 to 10,000 g/mol, 750 to 8,000 g/mol, or 1,000 to 6,000 g/mol, for example, 2,000 g/mol or 5,000 g/mol.

An alkyl chloroformate used in the present invention may be an aliphatic compound, and may be a chloroformate having a C4 to C10, C4 to C8, C6 to C10, or C8 to C10 alkyl group. For example, butyl chloroformate, octyl chloroformate, or dodecyl chloroformate may be used as an alkyl chloroformate, but the present invention is not limited thereto.

The polyethylene glycol-alkyl carbonate prepared by the above method may be confirmed by FT-IR and NMR assay.

2. Preparation of Micelle Particle Through Solvent Evaporation Method

The polyethylene glycol-alkyl carbonate which is a synthetic polymer prepared in the step 1 may be prepared into micelles through a solvent evaporation method.

The polyethylene glycol-alkyl carbonate may be dissolved in an organic solvent, and a solvent evaporation method may be carried out using nitrogen to volatilize the solvent. Afterward, the resulting substance may be dispersed again in an aqueous solution to prepare micelles. In one embodiment, 5 to 15 mg of polyethylene glycol-alkyl carbonate may be dissolved in an organic solvent. The organic solvent may be a commonly used organic solvent, for example, acetonitrile, methylene chloride, chloroform, or methanol.

3. Preparation of Micelle Particle Through Solvent Mixture Evaporation Method

The polyethylene glycol-alkyl carbonate which is a synthetic polymer prepared in the step 1 may be prepared into micelles through a solvent mixture evaporation method.

The polyethylene glycol-alkyl carbonate may be dissolved in a solvent mixture, and a solvent mixture evaporation method may be carried out using nitrogen to volatilize the solvent. Afterward, the resulting substance may be dispersed again in an aqueous solution to prepare micelles. In one embodiment, 5 to 15 mg of polyethylene glycol-alkyl carbonate may be dissolved in a solvent mixture. The solvent mixture may be a mixture of commonly used organic solvents, for example, a solvent mixture of methylene chloride and acetonitrile, a solvent mixture of methylene chloride and chloroform, or a solvent mixture of methylene chloride and methanol.

The solvent mixture used in the present invention may include methylene chloride and other solvents in a ratio of 3 to 1:1 to 3.

In addition, the micelle according to the present invention may have micelle particles of various sizes according to the type of a single solvent or a solvent mixture. In one embodiment, a single methylene chloride solvent or a solvent mixture of methylene chloride and chloroform (in a mixing ratio of 2:1) may be used to obtain micelles with a uniform size, but the present invention is not limited thereto.

Additionally, the micelle according to the present invention may generate a varying amount of gas according to the type of a single solvent or a solvent mixture. In one embodiment, a solvent mixture of methylene chloride and acetonitrile (2:1) or a solvent mixture of methylene chloride and chloroform (2:1) may be used to generate a large amount of carbon dioxide gas, and particularly, a solvent mixture of methylene chloride and acetonitrile (2:1) may be used to generate a larger amount of gas after 1 hour.

The gas-generating micelles according to the present invention are circulated in the body and deposited on the disease site to generate carbon dioxide, and thus a more enhanced ultrasonic diagnostic image can be obtained.

EXAMPLES

Hereinafter, the present invention will be described in further detail with reference to examples thereof. It should be clear to those skilled in the art that the following examples are merely presented to exemplify the present invention, and the scope of the present invention is not limited to the following examples.

<Example 1> Experimental Materials

Polyethylene glycol was purchased from Sigma-Aldrich Co. and used. Available polyethylene glycol has a number average molecular weight (Mn) of 550 to 20,000. Among them, polyethylene glycol having a number average molecular weight of 2,000 to 5,000 is preferable to prepare a gas-generating polymeric micelle and thus was used in this experiment.

As an alkyl chloroformate, butyl chloroformate and octyl chloroformate, which are aliphatic compounds, were purchased from Sigma-Aldrich Co., and dodecyl chloroformate was purchased from Santa Cruz Biotechnology.

<Example 2> Synthesis of Polyethylene Glycol-Alkyl Carbonate (Synthetic Polymer)

The polyethylene glycol and alkyl chloroformate which were prepared in Example 1 were separately dissolved in acetonitrile. Specifically, 0.5 mmol of polyethylene glycol was dissolved in 4 ml of acetonitrile to prepare a polyethylene glycol solution, and 2 mmol of an alkyl chloroformate was added to 5 ml of acetonitrile to prepare an alkyl chloroformate solution.

The alkyl chloroformate solution was added to the polyethylene glycol solution, and the mixture was stirred for 5 minutes. To the mixture thus stirred, 2.5 mmol of pyridine was added and reacted at 0° C. for 30 minutes and then at room temperature for 24 hours. The resulting solution was precipitated in diethyl ether, filtrated, and then dried in a vacuum dryer for 3 days to obtain polyethylene glycol-alkyl carbonate which is a synthetic polymer.

Various types of polyethylene glycol-alkyl carbonate (synthetic polymer) may be prepared according to a number average molecular weight of polyethylene glycol and a type of alkyl in the alkyl chloroformate. For example, when polyethylene glycol having a number average molecular weight of 5,000 and octyl chloroformate were used, polyethylene glycol5000-octyl carbonate was prepared, which may also be expressed as mPEG5000-8 and mPEG5000-octyl carbonate.

<Example 3> Confirmation of Polyethylene Glycol-Alkyl Carbonate Synthesis

In the preparation of polyethylene glycol-alkyl carbonate according to Example 2, coupling between polyethylene glycol and the alkyl carbonate was confirmed by a FT-IR spectrometer (Nicholet iS50, Thermo) and NMR600 (VNMRS 600 MHz, VARIAN).

The introduction of a carbonate linkage in polyethylene glycol-alkyl carbonate was analyzed by FT-IR. As a result, it was confirmed that the carbonate linkage was present in polyethylene glycol-alkyl carbonate at a wavenumber of 1,746 cm-1 (FIGS. 2 and 3).

In addition, it was confirmed through NMR assay that the OH peak (1.86 ppm) observed in polyethylene glycol disappeared, or the intensity thereof was lowered, in polyethylene glycol-alkyl carbonate, and the synthesized polyethylene glycol-alkyl carbonate exhibited new peaks at 1.64 ppm, 1.40 ppm, and 0.92 ppm (FIGS. 4 and 5).

<Example 4> Confirmation of Generation of Carbon Dioxide Gas by Hydrolysis of Polyethylene Glycol-Alkyl Carbonate The polyethylene glycol-alkyl carbonate which is a synthetic polymer prepared in Example 2 was dissolved in Dulbecco's phosphate-buffered saline (DPBS), and then generation of carbon dioxide gas by hydrolysis of the synthetic polymer was confirmed by observing generated bubbles (FIG. 6). As a result, it was confirmed that the largest amount of bubbles caused by carbon dioxide was generated by a synthetic polymer to which a dodecyl carbonate group was introduced, and an amount of bubbles generated decreases in the order of an octyl carbonate and a butyl carbonate (FIG. 7). That is, it was confirmed that a longer chain of alkyl carbonate caused generation of a larger amount of carbon dioxide gas.

In addition, the polyethylene glycol-alkyl carbonate according to Example 2 was dissolved in tertiary distilled water, then maintained at 37° C. for 24 hours, and freeze-dried. Afterward, the resulting substance was analyzed by 1H-NMR. As a result, it was confirmed that the OH peak (1.86 ppm) of polyethylene glycol, which had disappeared when polyethylene glycol-alkyl carbonate was synthesized, was regenerated by hydrolysis. From this result, it was confirmed that when polyethylene glycol had a smaller number average molecular weight and a longer-chain alkyl carbonate group was introduced, the area of an OH peak regenerated by hydrolysis increased, which shows the same pattern as the amount of carbon dioxide gas generated in an aqueous solution (dodecyl>octyl>butyl) (FIGS. 8 and 9).

<Example 5> Preparation of Micelle Particles Through Solvent Evaporation Method

Micelles were prepared through a solvent evaporation method using an organic solvent such as acetonitrile, methylene chloride, chloroform, or methanol. 10 mg of the synthetic polymer (prepared in Example 2) was dissolved in each of the above-described organic solvents, a solvent evaporation method was carried out using nitrogen to volatilize the solvent, and then the resulting substance was dispersed again in an aqueous solution to prepare micelles.

As a result of preparing micelles using 100% methylene chloride as an organic solvent, micelles with a size of 166 nm to 202 nm were prepared. The micelles were dispersed again in an aqueous solution to generate a small amount of carbon dioxide, which was confirmed through optical imaging (FIG. 10).

TABLE 1

The size of micelle particles prepared using 100% methylene chloride as organic solvent

| | Size (nm) | PDI |
|---|---|---|
| mPEG2000-butyl carbonate | 166 ± 5 | 0.13 ± 0.02 |
| mPEG2000-octyl carbonate | 202 ± 13 | 0.21 ± 0.05 |
| mPEG2000-dodecyl carbonate | 135 ± 3 | 0.33 ± 0.01 |
| mPEG5000-butyl carbonate | 196 ± 11 | 0.11 ± 0.02 |
| mPEG5000-octyl carbonate | 182 ± 2 | 0.12 ± 0.03 |
| mPEG5000-dodecyl carbonate | 196 ± 11 | 0.14 ± 0.01 |

<Example 6> Preparation of Micelle Particles Through Solvent Mixture Evaporation Method Micelle particles were prepared using polyethylene glycol5000-dodecyl carbonate, in which the largest amount of gas was generated according to the result of Example 5, as a synthetic polymer and various solvent mixtures. A solvent mixture evaporation method was carried out using solvent mixtures including methylene chloride and acetonitrile, chloroform, or methanol in a ratio of 2:1, 1:1, or 1:2 to prepare micelle particles.

An amount of gas generated by polyethylene glycol5000-dodecyl carbonate micelle particles was confirmed through optical imaging. As a result, it was confirmed that a much greater amount of gas was generated by micelle particles prepared using chloroform alone or a solvent mixture of methylene chloride and chloroform than by micelle particles prepared using other solvents (FIG. 11).

As a result of size and stability evaluation through the micelle particle analysis, it was confirmed that micelle particles with a uniform size cannot be prepared except for the cases of using methylene chloride as a single solvent or a solvent mixture of methylene chloride and chloroform (in a mixing ratio of 2:1).

Therefore, based on the optical imaging and the result of particle analysis, the solvent mixture of methylene chloride and chloroform (2:1) was finally selected as a solvent for preparing micelle particles and used in the subsequent experiment.

<Example 7> Preparation of Micelle Particles Using Solvent Mixture of Methylene Chloride and Chloroform (2:1)

The sizes of micelle particles prepared using the solvent mixture of methylene chloride and chloroform (2:1) derived in Example 6 were measured. As a result, it was confirmed that the micelle particles had a size of 203 nm to 472 nm, which was a wider size range than that of the micelle particles prepared using 100% methylene chloride (Table 2).

TABLE 2

The size of micelle particles prepared using solvent mixture of methylene chloride and chloroform (2:1)

| | Size (nm) | PDI |
|---|---|---|
| mPEG2000-butyl carbonate | 235 ± 8 | 0.21 ± 0.04 |
| mPEG2000-octyl carbonate | 472 ± 62 | 0.30 ± 0.13 |
| mPEG2000-dodecyl carbonate | — | — |
| mPEG5000-butyl carbonate | 203 ± 44 | 0.35 ± 0.12 |
| mPEG5000-octyl carbonate | 256 ± 18 | 0.13 ± 0.03 |
| mPEG5000-dodecyl carbonate | 405 ± 41 | 0.35 ± 0.03 |

<Example 8> Measurement of Ultrasonic Diagnosis Capacity of Micelle Particle Prepared Using Solvent Mixture of Methylene Chloride and Chloroform (2:1)

The ultrasonic diagnosis capacity of a gas-generating micelle was evaluated using ultrasound equipment (Vevo 770; Visualsonics). As a result, it was confirmed that polyethylene glycol5000-dodecyl carbonate exhibited an ultrasound imaging effect superior to that of other synthetic polymers (FIG. 12).

As a quantitative analysis result of an ultrasound image, a micelle prepared using a synthetic polymer to which a dodecyl carbonate group was bound exhibited a high contrast ultrasound imaging effect compared to micelles in which other alkyl carbonate groups were bound. In particular, polyethylene glycol5000-dodecyl carbonate produced a contrast ultrasound imaging effect within 1 hour that was greater by 5 to 10-fold compared to other synthetic polymers (FIG. 13).

<Example 9> Verification of Controllability of Amount and Characteristics of Gas Generated by Polyethylene Glycol-Alkyl Carbonate Prepared Through Solvent Mixture Method Polyethylene glycol2000-octyl carbonate was prepared into micelles through a solvent mixture method. In this case, a solvent mixture of methylene chloride and acetonitrile (2:1), a solvent mixture of methylene chloride and chloroform (2:1), and a solvent mixture of methylene chloride and methanol (2:1) were used as a solvent mixture. The micelles prepared using the above-described various solvent mixtures generated a varying amount of gas according to the type of an organic solvent mixture. It was confirmed that when a solvent mixture of methylene chloride and acetonitrile (2:1) and a solvent mixture of methylene chloride and chloroform (2:1) were used, a large amount of carbon dioxide gas was generated. Particularly, when a solvent mixture of methylene chloride and acetonitrile (2:1) was used, a larger amount of gas was generated after 1 hour had elapsed. These results show that a time for which gas is generated by a micelle and an amount of gas generated may be adjusted by varying a type of a solvent mixture (FIG. 14).

<Example 10> Cytotoxicity Assay of Micelles

The cytotoxicities of polyethylene glycol-alkyl carbonate itself and micelles prepared using the polymer and a solvent mixture of methylene chloride and chloroform (2:1) as a solvent were evaluated using HeLa cells. As a result, it was confirmed that there was no significant difference between polyethylene glycol-alkyl carbonate or micelles based thereon and a control in which no treatment was performed, indicating that polyethylene glycol-alkyl carbonate and micelles based thereon have low toxicity (FIG. 15).

<Example 11> Ligand-Specific Transmission Capacity Assay of Micelles

Ligand-bound micelles were prepared and observed through fluorescence imaging.

The ligand-bound micelles were prepared as follows.

First, aminopolyethylene glycol having an amino group reacted with a ligand in a molar ratio of 1:1 through an EDC/NHS reaction to prepare ligand-bound polyethylene glycol. Afterward, the ligand-bound polyethylene glycol was dialyzed for 4 days, filtrated with a 0.2 um filter, and then freeze-dried. The ligand-bound (-introduced) polyethylene glycol reacted with an alkyl chloroformate through the method of Example 2 to prepare ligand-introduced polyethylene glycol-alkyl carbonate (synthetic polymer). Afterward, the ligand-introduced polyethylene glycol-alkyl carbonate and polyethylene glycol-alkyl carbonate were used in a weight ratio of 1:10 to prepare micelles. In this case, a solvent mixture of methylene chloride and chloroform (2:1) was used as a solvent.

Meanwhile, Cy5.5 (fluorescent substance)-introduced polyethylene glycol-alkyl carbonate and micelles were prepared in the same manner as in the preparation of ligand-introduced polyethylene glycol-alkyl carbonate except that Cy5.5 was used instead of a ligand, and a weight ratio of 1:100 was used in the preparation of micelles.

HepG2 cells were incubated at a density of 1×105 cells/well in a confocal dish and treated with the Cy5.5-introduced micelles. The medium was removed after 2 hours, and the resulting cells were washed with PBS three times and then fixed with 4% formaldehyde. The cells were stained with DAPI, then mounted, and observed through a fluorescence microscope (TE2000-E; Nikon).

As a result of observation through a fluorescence microscope, it was confirmed that the cells treated with RGD ligand-introduced micelles produced a red fluorescence signal with high intensity, indicating that an intracellular transmission capacity is improved due to the introduction of a ligand (FIG. 16).

In addition, fluorescence intensity was quantified using ImageJ software (National Institutes of Health) to quantify the result observed with the naked eye. As a result, it was confirmed that RGD ligand-bound micelles (RGD-PEG2000-8 and RGD-PEG5000-8) had intracellular transmission capacities improved by 7 to 11-fold compared to micelles without a ligand.

<Example 12> Cell Death Effect Assay of Drug-Carrying Micelles

Doxorubicin (DOX), which is a drug, was carried in polyethylene glycol-alkyl carbonate micelles, and then a cell death effect of the micelles was evaluated.

Drug-carrying micelles consisting of a drug (DOX) and polyethylene glycol-alkyl carbonate (1:99) were prepared using methylene chloride including a dissolved drug, through a solvent mixture evaporation method (using methylene chloride and chloroform (2:1) as a solvent mixture).

HepG2 cells were incubated at a density of 1×105 cells/well in a 12-well plate, treated with various concentrations (0.01 to 1 mg/ml) of the drug-carrying micelle, and then incubated at 37° C. under 5% CO2 for 12 hours. The medium was removed after 12 hours, and the resulting cells were washed with PBS once and then incubated in DMEM (supplemented with 10% FBS and 1% penicillin/streptomycin) for 36 hours. The cells were washed with PBS three times, and each well was treated with a MTT solution (50 ug/ml) for 2 hours.

The formazan crystals thus produced were dissolved in DMSO, and the light absorbance thereof was measured with a UV/Visible spectrophotometer at 540 nm.

As a result, it was confirmed that drug-carrying micelles (PEG5000-8-DOX and RGD-PEG5000-8-DOX) had 3.32 to 5.47-fold cell death effects compared to a group in which a drug was not loaded.

In particular, it was confirmed that when a drug was carried in a ligand-bound micelle, a cell death effect was more excellent (FIG. 18).

While the present invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method of preparing a gas-generating micelle including a compound represented by the following Formula 1, the method comprising: mixing polyethylene glycol and an alkyl chloroformate to synthesize a polyethylene glycol derivative; wherein the polyethylene glycol derivative is represented by Formula I, and dissolving the polyethylene glycol derivative in one solvent selected from acetonitrile, methylene chloride, chloroform, and methanol or in a solvent mixture of two or more selected therefrom and then evaporating the solvent(s), and then dispersing the polyethylene glycol derivative in an aqueous solution,

[Formula 1]

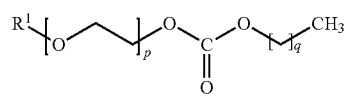

wherein $R^1$ is a C1 to C2 alkyl group, H, —$NH_2$, or COOH, p is an integer ranging from 12 to 227,
q is an integer ranging from 2 to 14, and
wherein the micelle has a diameter of 150 to 500 nm.

2. The method according to claim 1, wherein the solvent mixture is prepared by mixing methylene chloride with acetonitrile, chloroform, or methanol in a mixing ratio of 3 to 1:1 to 3.

3. The method according to claim 1, wherein the polyethylene glycol has a number average molecular weight (Mn) of 550 to 10,000 g/mol.

* * * * *